US009133563B2

(12) United States Patent
Andreacchi

(10) Patent No.: US 9,133,563 B2
(45) Date of Patent: Sep. 15, 2015

(54) ELECTROPOLISHING DEVICE AND METHOD

(75) Inventor: Anthony S. Andreacchi, San Jose, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 246 days.

(21) Appl. No.: 13/618,407

(22) Filed: Sep. 14, 2012

(65) Prior Publication Data

US 2014/0076739 A1    Mar. 20, 2014

(51) Int. Cl.
 *C25F 3/16* (2006.01)
 *C25F 7/00* (2006.01)

(52) U.S. Cl.
 CPC .... *C25F 3/16* (2013.01); *C25F 7/00* (2013.01)

(58) Field of Classification Search
 CPC .................................. C25F 3/16; C25F 7/00
 USPC ....................................................... 204/242
 See application file for complete search history.

(56) References Cited

U.S. PATENT DOCUMENTS

| | | | |
|---|---|---|---|
| 4,127,459 | A | 11/1978 | Jumer |
| 7,208,070 | B2 | 4/2007 | Swain |
| 7,252,746 | B2 | 8/2007 | Schaeffer |
| 2004/0267351 | A1 | 12/2004 | Swain |
| 2005/0098444 | A1 | 5/2005 | Schaeffer |
| 2007/0034527 | A1 | 2/2007 | Diaz et al. |
| 2007/0034528 | A1 | 2/2007 | Diaz et al. |
| 2007/0156215 | A1* | 7/2007 | Jensen et al. ................. 607/116 |
| 2007/0209947 | A1 | 9/2007 | Shrivastava et al. |
| 2008/0312747 | A1 | 12/2008 | Cameron et al. |
| 2009/0255827 | A1* | 10/2009 | Andreacchi et al. .......... 205/640 |
| 2011/0247943 | A1 | 10/2011 | Bialas et al. |
| 2012/0199489 | A1 | 8/2012 | Vacheron |
| 2014/0360887 | A1 | 12/2014 | Andreacchi et al. |

FOREIGN PATENT DOCUMENTS

JP    H0790694    4/1995

OTHER PUBLICATIONS

U.S. Appl. No. 13/618,348, filed Sep. 14, 2012, Andreacchi et al.
U.S. Appl. No. 13/617,877, filed Sep. 14, 2012, Andreacchi et al.
U.S. Appl. No. 13/618,455, filed Sep. 14, 2012, Andreacchi et al.
U.S. Appl. No. 13/618,348, Dec. 19, 2013, Office Action.
U.S. Appl. No. 13/617,877, Dec. 20, 2013, Office Action.
U.S. Appl. No. 13/618,348, Apr. 16, 2014, Notice of Allowance.
U.S. Appl. No. 13/617,877, Apr. 18, 2014, Office Action.
U.S. Appl. No. 13/617,877, Sep. 23, 2014, Office Action.
U.S. Appl. No. 13/618,455, May 8, 2014, Office Action.
U.S. Appl. No. 13/618,455, Sep. 25, 2014, Office Action.
U.S. Appl. No. 13/618,455, Feb. 2, 2015, Notice of Allowance.

* cited by examiner

*Primary Examiner* — Nicholas A Smith
(74) *Attorney, Agent, or Firm* — Workman Nydegger; John Kwok

(57) ABSTRACT

A device for repositioning a device during an electropolishing process. A fixture is disclosed that is configured to reposition the device during the electropolishing process in order to more evenly electropolish a surface of the device.

17 Claims, 8 Drawing Sheets

ELECTROPOLISHING DEVICE AND METHOD

BACKGROUND OF THE INVENTION

Medical devices are an important part of the health industry and responsible for saving many lives. There are many procedures that can be performed today because of advances in medical device technology. Stents, for instance, are examples of medical devices that are used in a variety of medical procedures. When stents are used in the context of the vascular system, they can open blocked vessels, increase the flow of blood, and prevent reoccurrence of the blockage. Stents are often used to address weak points or blocked sections of a patient's vasculature. Stents are not limited, however, to the vasculature system and can be employed in many different systems and circumstances.

The production of medical devices such as stents can be a complicated process. Producing the stent includes forming struts that are arranged to provide strength and flexibility to the stent. The struts can be formed, for example, by laser cutting. Once the stent is formed, the stent is then polished. The stent is polished in order to remove rough edges that may remain on the stent and to smooth the surface of the stent. As one can image, a stent with rough edges may have adverse effects if introduced into a patient's vasculature. The stent could cut a vessel's wall or become inadvertently displace, for instance. Rough regions on the stent's surface may create potential areas for thrombogenesis or may negatively impact tissue.

One method of polishing the stent is by a process of electropolishing. Electropolishing stents is a common process that is usually performed in an electrolytic bath. In conventional systems, however, maintaining a consistent surface finish, particularly along the inner surface of the stent, can be difficult. More specifically, electropolishing stents requires contact between the stent and an electrode. The contact between the electrode and the stent surface impede polishing at the contact points. As a result, the stent is polished at a different rate at or near the contact points than at other areas of the stent. There is therefore a need for a way to minimize this effect in order to ensure that surface finish of the stent remains as consistent as possible throughout the electropolishing process.

BRIEF SUMMARY OF THE INVENTION

Embodiments of the invention relate to electropolishing devices including medical devices. Embodiments can achieve a more consistent surface finish of the device being electropolished by repositioning the device relative to an electrode during the electropolishing process. Repositioning the device during the electropolishing process exposes contact points between the electrode and the device to establish new contact points. Repositioning the device ensures that the previous contact points are more effectively subjected to the electropolishing process. Repositioning the device during the electropolishing process achieves a more consistent electropolished surface.

In an embodiment, a system for electropolishing a device includes an electrode (e.g., an anode) that is configured to contact the device at contact points, another electrode (e.g., a cathode), an electrolytic bath, and an electropolishing fixture (fixture). The anode, cathode, and device are immersed or submerged in the electrolytic bath. The fixture is configured to reposition the device while the device is immersed in the electrolytic bath and undergoing the electropolishing process. Repositioning the device exposes the old contact points more effectively to the electropolishing process. In other words, the contact points between the device and the anode are changed such that the contact points are more effectively electropolished.

The fixture may include a first grip, a second grip, and/or a controller. The grips are configured to engage a surface of the device with sufficient force to reposition the device without damaging the device. The controller controls the movement or positioning of the grips and is configured to move the grips in a manner that repositions the device relative to the anode. Repositioning the device establishes new contact points at an area of the device that have already undergone the electropolishing process. The previous contact points are exposed such that the previous contact points are more effectively electropolished.

A method for electropolishing a device includes placing the device on an anode, which contacts the device at one or more contact points. The device is then immersed in an electrolytic bath and the device is electropolished. For example, a current may pass from the anode to the cathode through the device and the electrolytic bath. The device is repositioned during the electropolishing process. Once the device is electropolished, the device is removed from the electrolytic bath and unloaded from the anode.

These and other advantages and features of the present invention will become more fully apparent from the following description and appended claims, or may be learned by the practice of the invention as set forth hereinafter.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope.

The invention will be described and explained with additional specificity and detail through the use of the accompanying drawings in which.

DETAILED DESCRIPTION OF THE PREFERRED EMBODIMENTS

Embodiments of the invention relate to systems and methods for electropolishing devices including medical devices. More particularly, embodiments relate to systems and methods for adjusting a position of a medical device while the device undergoes an electropolishing process or to changing the contact points between the device and an electrode during the electropolishing process. Adjusting the position of the medical device can alleviate situations where the electropolishing process is impeded or proceeds at a slower rate. Although embodiments are discussed with reference to a medical device and more particularly in the context of a stent, embodiments are applicable generally to electropolishing systems and methods and to the electropolishing of other devices including other medical devices.

Embodiments provide systems and methods for automatically and/or manually repositioning a device while the device is immersed within an electropolishing bath, such as an electrolytic bath. An electropolishing fixture (fixture) is configured to engage with or contact the device in order to reposition the device in the electropolishing bath. In another example, the fixture may move the electrode relative to the device. Repositioning the device (or electrode) changes the contact points between the device and the electrode and enables previous contact points to undergo the electropolishing process at a faster rate. Advantageously, the finish of the device is improved.

The fixture may include grips that are capable of relative movement while contacting the device. The relative movement of the grips repositions the device. Advantageously, areas or locations of the device that may have been covered by or in contact with the grips or that may have been in covered by or in contact with an anode and/or cathode are exposed in the electropolishing bath when the device is repositioned. As a result, the electropolishing of the device is improved and the electropolishing process produces a device to have, for instance, an improved surface finish.

Figure 1:
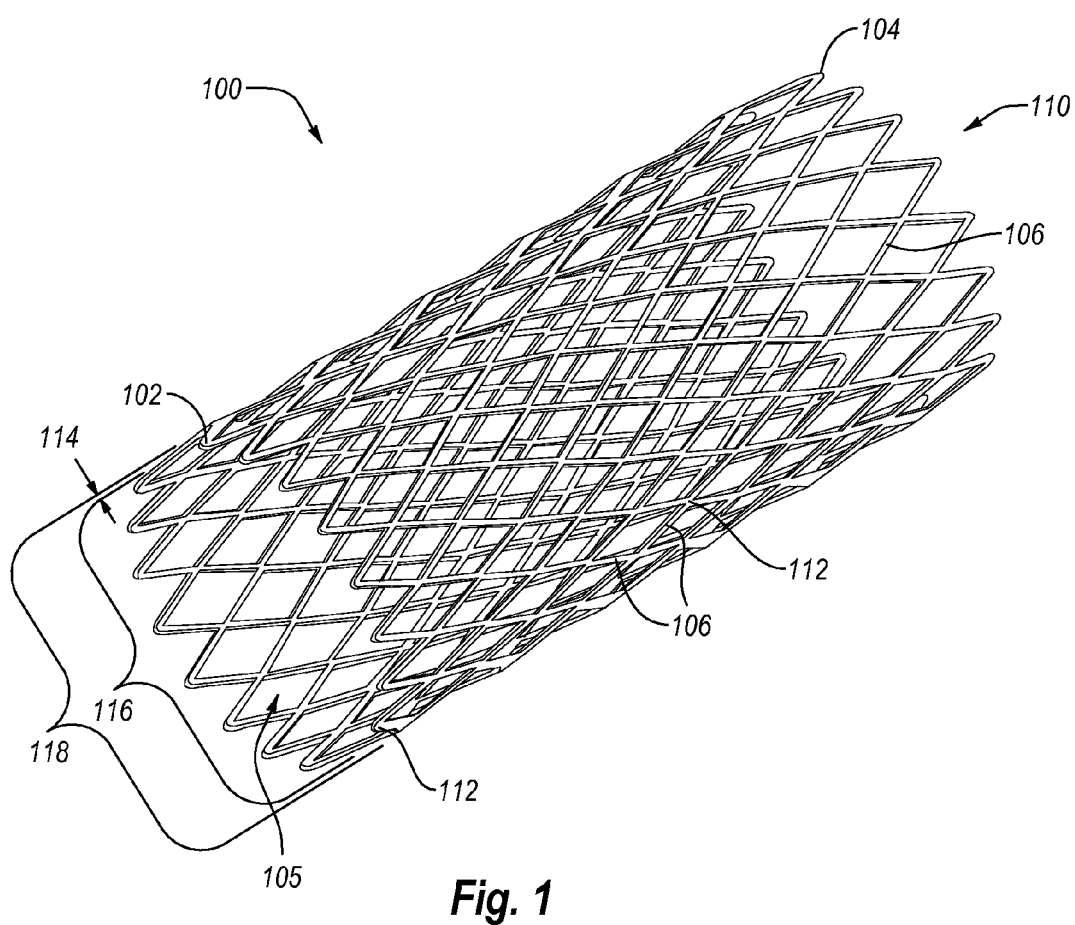
FIG. 1 illustrates a perspective view of a stent, which is an example of a medical device.

FIG. 1 illustrates a perspective view of an example medical device and is referred to herein as a stent 100. The stent 100 includes a body 110 that is generally tubular in shape, although other shapes and configurations are contemplated. The stent 100 has a first end 102 and a second end 104 that oppose each other or that are on opposing ends of the body 110 and a lumen 105 extending therethrough. The body 110 includes struts 106 that are arranged to provide, by way of example only, strength and flexibility to the stent 100.

The stent 100 may also have a thickness 114, an inner diameter 116 and an outer diameter 118. The difference between the inner diameter 116 and the outer diameter 118 may define the thickness 114 of the stent 100. Embodiments of the invention can more evenly polish the stent 100 such that at least some dimensions, such as the thickness 114 of the body 110 or the dimensions of the struts 106 are more uniform. Embodiments of the invention also help prevent rough regions from remaining on the stent's surface after the electropolishing process is completed.

The stent 100 may be made of a material or alloy including, but not limited to, Nitinol, stainless steel, cobalt chromium, or the like. The stent 100 has certain characteristics that facilitate operation of the stent. Some embodiments of the stent 100 (e.g., a stent formed of Nitinol) may be deformed (e.g., bent, compressed, expanded, or the like) by a force. When the force is removed, the stent 100 returns to its original shape. The elasticity and deformability of the stent 100 aid in the deployment of the stent 100 as well as in the operation of the stent 100.

While manufacturing the stent 100, the formation of the struts 106 or of the ends 102, 104 often results in edges 112 or other areas that are rough or unsmooth. In fact, the surface of the stent 100 is often rough. One purpose of electropolishing the stent 100 is to smooth the edges 112 as well as the surface of the stent 100. Polishing the stent 100 can smooth the edges 112 and the surface (inner and outer) to facilitate operation of the stent 100. This may prevent the stent 100 from having problems during deployment and from causing problems to the vasculature or tissue once deployed.

Figure 2:
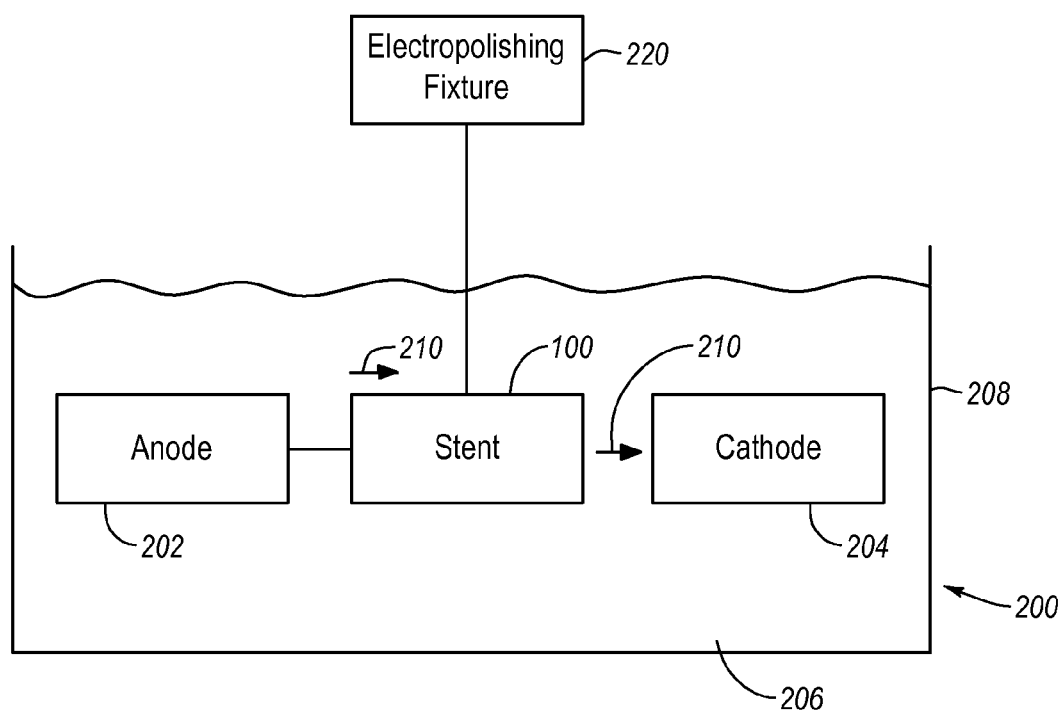
FIG. 2 illustrates an example block diagram of a system for performing an electropolishing process on devices including medical devices.

FIG. 2 illustrates a block diagram of an example system 200 for electropolishing the stent 100 or other device. More specifically, the stent 100 can be electropolished in the system 200. The system 200 includes a container 208 that holds an electrolytic bath 206. The system 200 electropolishes the stent 100 in the electrolytic bath 206.

During the electropolishing process, the stent 100 is usually fully immersed in the electrolytic bath 206 along with an anode 202 and a cathode 204. The anode 202 and/or cathode 204 may or may not be fully immersed in the bath 206. However, the stent 100 or other device is typically fully immersed in the electrolytic bath 206. Prior to immersion in the electrolytic bath 206, the stent 100 is positioned such that the stent 100 comes into contact with the anode 202. In other words, the stent 100 is loaded onto the anode 202 or otherwise placed into contact with the anode 202. The fixture 220 may be configured such that the stent 100 can be removed from and immersed in the electrolytic bath 206. More generally, the fixture 220 is configured to be positioned within and withdrawn from the electrolytic bath 206. For example, the stent 100 may be loaded on the anode 202 outside of the electrolytic bath 206 and then immersed in the bath 206 for the electropolishing process. The fixture 220 may be mounted on a frame that enables the fixture 220 to be operated such that the stent 100 can be immersed and withdrawn from the bath 206 as needed.

Once the stent 100 is immersed in the bath 206, a current 210 is then applied. The current 210 flows from the anode 202 to the cathode 204 through the stent 100 and the electrolytic bath 206. In this manner, the stent 100 is electropolished.

More specifically, electropolishing uses electrochemical reactions to remove material from a stent or device surface. Electropolishing tends to remove stent material that has increased electrical current densities. Portions of the stent's surface that are rough (bumps, shards, etc.) tend to have higher electrical current densities and are thus removed during the electropolishing process. The surface of the stent 100 is smoothed and polished by the removal of material from the stent's surface.

The system 200 includes a fixture 220 that is configured to reposition the stent within the electrolytic bath 206. The fixture 220 can be controlled automatically and/or manually to reposition the stent 100 within the electrolytic bath 206. The fixture 220 may be contained wholly or partially within the container 208. Alternatively, the fixture 220 may be located outside of the container 208 as illustrated in FIG. 2.

During the electropolishing process performed in the system 200, the stent 100 is typically in contact with an electrode such as the anode 202. As a result, the anode 202 establishes contact points between the anode 202 and the surface of the stent 100. The anode 202 can be configured with one or more contact points and the contact points can be on the internal surface of the stent 100 and/or an external surface of the stent 100. In one example, the anode 202 contacts only an internal surface of the stent 100.

Current is supplied to the stent 100 through the anode 202. The cathode 204 is electrically connected with the stent 100 via the electrolytic bath 206. As a result, current flows to the cathode 204 through the electrolytic bath 206. Current flow from the surface of the stent 100 is facilitated in this manner in order to remove material from the stent 100 and thereby smooth the stent surface during the electropolishing process. Contact points or more generally contact regions corresponding to the locations of contact between the stent 100 and the anode 202 have little or no current flow from the stent surface into the electrolytic bath 206. As a result, the stent's surface is not smoothed or polished in conventional systems or is not smoothed or polished at the same rate as other areas of the stent's surface.

The fixture 220 is configured to reposition the stent 100 to expose the contact regions such that the contact regions electropolish at an appropriate rate. Exposing the contact regions and establishing new contact regions by repositioning the stent 100 enables current to flow from the old contact regions into the electrolytic bath 206. As a result, the surface of the stent is more evenly smoothed by automatically and/or manually repositioning the stent 100 during the electropolishing process. Embodiments of the invention contemplate repositioning the stent 100 and/or the contact regions. Rotating the stent 100 while holding the anode 202 stationary repositions the contact regions.

In addition, repositioning the stent 100 can also result in a stent having better or more uniform dimensions. Repositioning the stent 100 can remove bumps or other portions of the stents' surface that may be rough, resulting in more even dimensions.

FIG. 2 thus illustrates the stent 100 positioned on the anode 202 or having contact with the anode 202. The anode 202 supplies current to the stent 100 during the electropolishing process. The stent 100 benefits from being repositioned while immersed within the electrolytic bath 206. Repositioning the stent 100 while the stent 100 is immersed exposes the stent 100 to a less oxidizing environment and ensures more even erosion of the stent material during the electropolishing process. In one example, the stent 100 remains immersed during the electropolishing process and thus does not need to be removed from the bath 206 to be repositioned, which results in less exposure to an oxidizing atmosphere.

Figure 3:
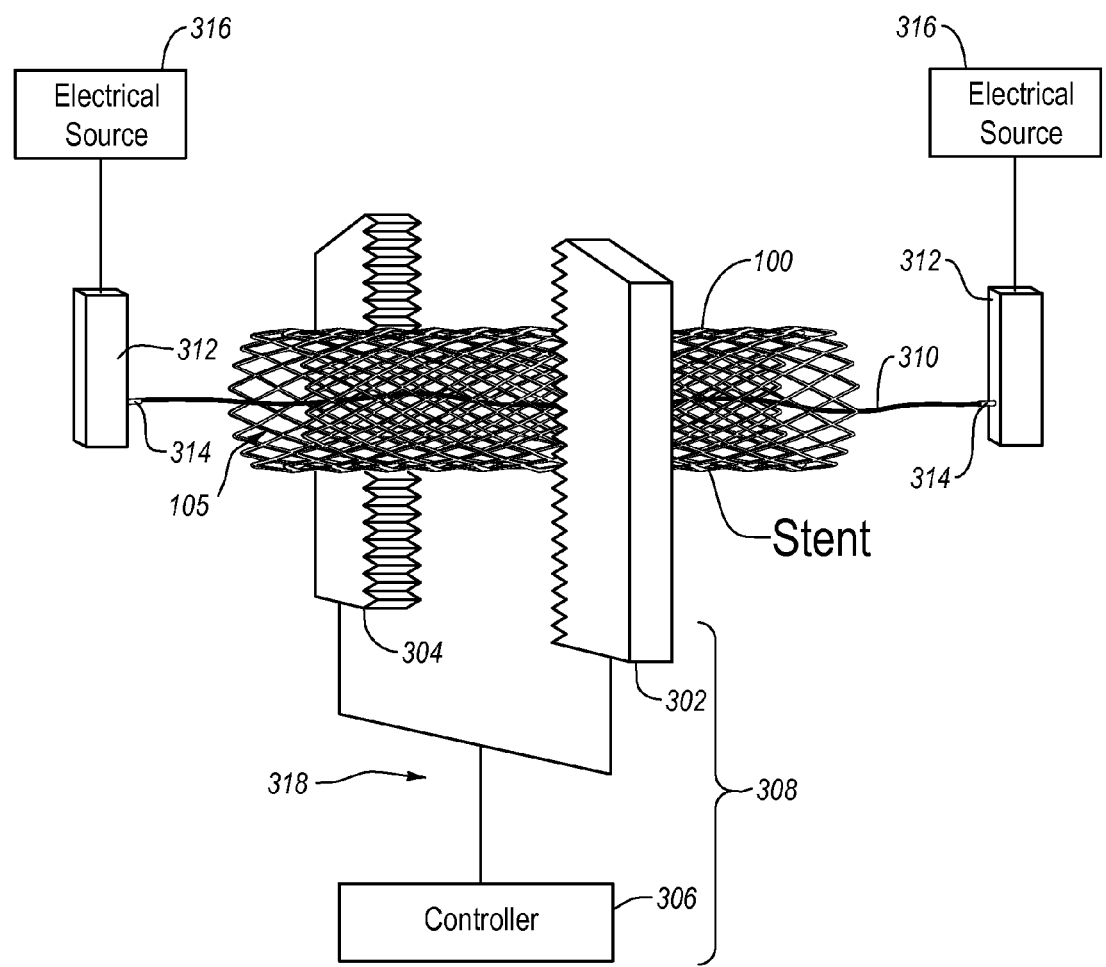
FIG. 3 illustrates a perspective view of a fixture configured to reposition a stent during an electropolishing process.
Figure 5:
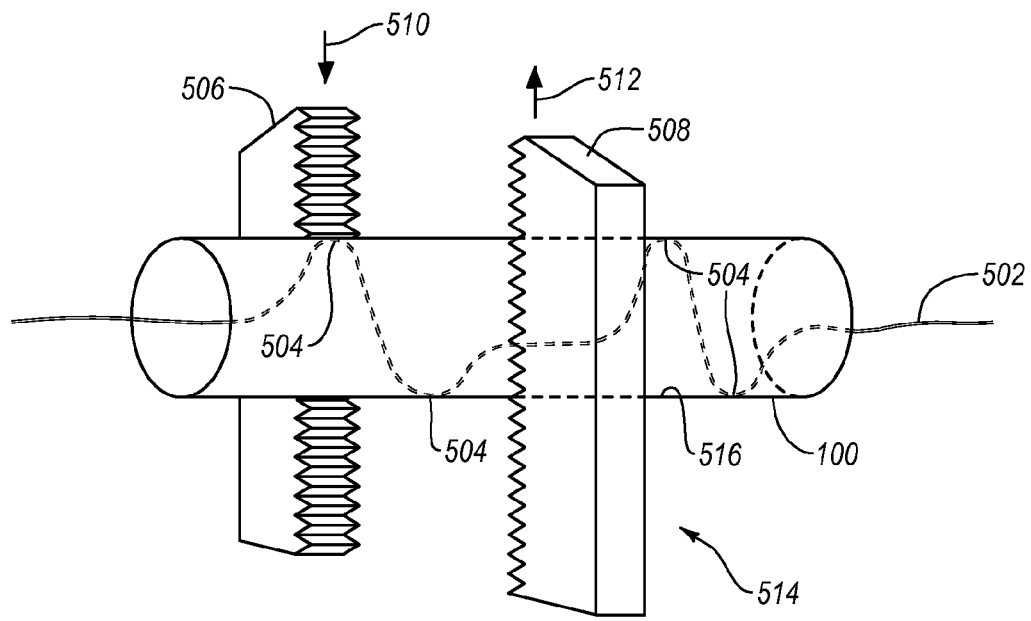
FIG. 5 is a side view illustrating another orientation of grips that are configured to reposition the stent and a view of contact points between an anode and the stent.

FIG. 3 illustrates a perspective view of a fixture 308 configured for repositioning the stent 100. The fixture 308 is an example of the fixture 220. In this example, the stent 100 is mounted or placed on an anode 310, which is an example of the anode 202. The anode 310 may also function as a mandrel for securing or holding the stent 100 within the electrolytic bath. In this example, the anode 310 is configured such that electrical contact is established between the anode 310 and the stent 100. Although the anode 310 is illustrated as a wire, the anode 310 may have curves or other geometries that may be as large as or slightly larger than the inner diameter of the stent 100. FIG. 5, for example, illustrates such an anode. This configuration ensures that electrical contact is established when the stent 100 is loaded on the anode 310.

The anode 310 may be removably secured to one or both posts 312 via contacts 314 and is configured to deliver a current to the stent 100. The posts 312 may have an inner conductor that enables the contacts 314 and the anode 310 to be connected with an electrical source 316, which may be a single electrical source that splits to connect electrically to both contacts 314. The posts 312, for example, may be part of the fixture 308 and can thus be withdrawn and immersed in the electrolytic bath. The posts 312 are configured to maintain a tension in the anode 310. The anode 310 may be stabilized in another suitable manner within the electrolytic bath. The anode 310 is arranged to pass through the lumen 105 of the stent 100. The anode 310 also contacts the inner surface of the stent 100 in this example.

More specifically, the anode 310 may be configured to position the stent 100 while contacting the inner surface of the stent 100 with a number of contact points. The anode 310, for example, may be shaped to hold the stent 100 and contact the inner surface of the stent 100 at one or more contact points.

The fixture 308 illustrated in FIG. 3 includes a controller 306 and grips 302 and 304. The grips 302 and 304 are placed, in this example, on opposing sides of the stent 100 and can be in contact with the exterior surface of the stent 100. Relative movement of the grips 302 and 304 can result in rotation of the stent 100 about the anode 310. In this example, the stent 100 is repositioned by rotating the stent 100 relative to the anode 310. Rotating the stent 100 changes the contact points between the anode 310 and the inner surface of the stent 100. The grips 302 and 304 may also be positioned to move the stent 100 laterally and/or rotationally. By repositioning the stent 100, previous contact points between the anode 310 and the inner surface of the stent 100 are exposed so as to be subjected to the electropolishing process.

The anode 310 is sized and configured to maintain contact between the anode 310 and the stent 100 before, during, and/or after repositioning. At the same time, the contact between the anode 310 and the stent 100 does not prevent rotation of the stent 100. The grips 302 and 304 are typically placed against the surface of the stent 100 so engage with the stent 100 to ensure rotation or repositioning of the stent 100. Alternatively, the grips 302 and 304 may be controlled to contact the stent 100 only when rotation or repositioning is desired. A linkage 318 may enable the controller 306 to move the grips 302 and 304 in multiple directions (up, down, radially, laterally, rotationally, etc.)

The grips 302 and 304 are examples of structure for repositioning the stent 100. The fixture 308 may include more grips. For example, the system 200 shown in FIG. 2 may be configured to electropolish many stents simultaneously. The controller 306 can control or reposition each stent individually and/or reposition all stents at the same time. Each stent, in this example, may be associated with one or more grips. Embodiments of the invention may be configured such that a single stent can be repositioned by one or more grips. In addition, the grips may be configured to reposition one or more stents at the same time.

For example, the controller 306 can control movement of the grip 302, the grip 304 or both of the grips 302 and 304 at the same time. In one example, one of the grips may be fixed and the controller 306 only controls movement of the other grip.

The controller 306 can be electrically and/or mechanically connected with the linkage 318 which capable of moving the grips 302 and 304. In this example, the grips 302 and/or 304 move vertically or substantially orthogonally to an axis (e.g., parallel to the anode 310) of the stent 100. For instance, once the grips 302 and 304 engage the surface of the stent 100, the grip 302 may move upward while the grip 304 moves downward. This relative movement repositions the stent 100. The grips 302 and 304 may also engage the stent 100 and then move the stent laterally to expose the contact points. The grips 302 and 304 may thus slide the stent 100 towards one of the posts 312.

During the electropolishing process, the stent 100 can be repositioned one or more times. During the electropolishing process, the stent 100 may be rotated less than a full rotation, a full rotation, or more than a full rotation. Repositioning the stent 100 may include lateral displacement and/or rotational displacement. The type of movement can be selected and controlled by the controller 306 and may depend on the configuration of the device being electropolished. The controller 306, for instance, may be programmed to reposition the stent 100 during the electropolishing process.

The grips 302 and 304 may be insulated, for example fabricated from PTFE. Furthermore, the grips 302 and 304 may remain in contact with the stent's surface or they may be pressed against the stent 100 only when stent repositioning is necessary. As shown in FIG. 3, rotation of the stent is accomplished by moving the grips 302 and 304 in opposite directions while the grips 302 and 304 are in contact with the stent's surface.

The surface finish of the stent 100 and features of the grips 302 and 304 can contribute to the rotation or repositioning of the stent 100. For example, the grips 302 and 304 may have teeth, waves, roughness, texture (e.g., hairlike) or other features or combination of features that help grip the stent surface. The features of the grips 302 and 304 may be able to fit between the struts of the stent 100 such that a rotational force can be exerted against at least the struts. At the same time, the grips 302 and 304 are configured such that the grips 302 and 304 do not adversely affect the finished surface of the stent 100 or otherwise damage the stent 100.

Movement of the grips 302 and 304 can be accomplished manually and/or automatically. Motors, pneumatic cylinders, linear actuators, or the like can be controlled with the controller 306 to permit rotation. As previously stated, the fixture 308 may be configured such that the grips 302 and 304 are always in contact with the stent or configured such that the grips 302 and 304 are only in contact with the stent's surface while rotation is required. The grips may be counterweighted in a manner that pushes the grips 302 and 304 against the stent's surface with sufficient force to enable the grips 302 and 304 to reposition the stent 100. As a result, the fixture 308 may be capable of moving the grips 302 and 304 in multiple directions and of orienting the grips in multiple orientations. In one example, the orientation and/or movement of the grip 302 can be controlled independently of the orientation and/or movement of the grip 304.

In another example, the anode 310 may be a non-conductive mandrel and current is delivered to the stent 100 via the grips 302 and 304. In this example, the grips 302 and 304 or, more specifically, at least a portion of the features (e.g., features 404 in FIG. 4) of the grips 302 and 304 are conductive and configured to deliver current to the outer surface of the stent 100. Rotation of the stent 100 changes the contact points between the stent 100 and the conductive portion of the grips 302 and 304 in this example and can ensure that the stent 100 has a more even finish.

Figure 4:
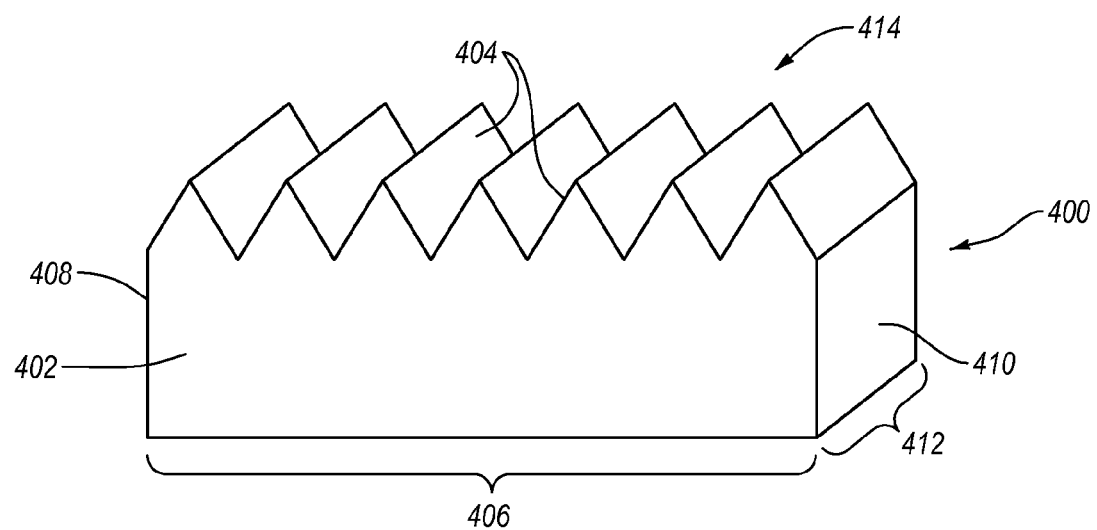
FIG. 4 illustrates a perspective view of a grip, which is included in an electropolishing fixture and is configured to engage with the stent in order to reposition the stent during an electropolishing process.

FIG. 4 illustrates a perspective view of a grip 400, which is an example of the grips 302 and 304. The grip 400 includes a body 402 and a first end 408 opposing a second end 410. A length 406 of the grip 400 is sufficient to permit adequate rotation or other movement or repositioning of the stent 100 during the electropolishing process. A width 412 of the stent is sufficient to ensure sufficient contact with the stent 100 while repositioning the stent 100.

The grip 400 includes a gripping surface 414 that includes features 404. The gripping surface 414 is configured to contact the stent when repositioning is performed. The features 404 are configured to ensure that the stent 100 is repositioned. The features 404 of the surface 414 may include, by way of example and not limitation, teeth, waves, roughness, or the like or any combination thereof or any other features capable of adequately engaging the stent's surface to enable rotation of the stent 100. The features 404 can be uniform, non-uniform, angled, or the like. The features 404 can be soft such that the features 404 deform when placed into contact with the stent 100. Alternatively, the features 404 may not deform. The features 404 may have a concave aspect that may increase the surface with which the features 404 engage the surface of the stent 100.

FIG. 5 further illustrates an example of a fixture 514 that includes grips 506 and 508, which are examples of the grips 302, 304, and/or 400. FIG. 5 illustrates that the grips 506 and 508 can be oriented in different manners relative to the stent 100. The grips 506 and 508 can be angled relative to the stents 100 or in another orientation. Typically, the grip 506 and the grip 508 have the same orientation relative to the stent 100. However, the grips 506 and 508 are not required to have the same orientation. For example, rotation or repositioning of the stent 100 can be achieved when one of the grips is held stationary while the other grip is moved to rotate or reposition the stent 100. FIG. 5 illustrates an example of how the grips 506 and 508 may be moved. In one example, the grip 506 moves in a direction 510 while the grip 508 moves in a direction 512. Movement of the grips 506, 508 in the directions, respectively, 510, 512, rotates the stent 100 about the anode 502.

FIG. 5 also illustrates an anode 502, which is an example of the anode 202, 310 or other electrode. During the electropolishing process, the stent 100 is placed on the anode 502. The anode 502 is shaped so as to come into contact with the stent 100. In FIG. 5, the anode 502 contacts an inner surface of the stent 100 at contact points 504. The number of contact points 504 can vary and may depend on the shape of the anode 502. The anode 502, for example, may be configured to have any number of contact points 504 with the stent 100 and more particularly with an inner surface 516 of the stent 100. The anode 502 may be planar such that the contact points 504 are in the same plane. Alternatively, the contact points 504 may not be arranged in the same plane. Thus, the anode 502 can have a variety of configurations and shapes.

The rotation or repositioning of the stent 100 can be performed such that the contact between the grips 506 and 508 and the stent 100 does not repeat during the electropolishing process. In other words, repositioning of the stent occurs in a manner such that for a given contact point, the contact point is not repeated for that stent during the electropolishing process. Each contact point is only a contact point one time. This can be the case for the contact points 504 between the stent and the anode and/or for the contact points between the grips and the outer surface of the stent. Embodiments may ensure that contact points between the anode 502 and the inner surface 516 are not repeated during the electropolishing process.

In one example, the anode 502 may simply be a non-conductive mandrel configured to hold the stent 100. In this example, the grips 506 and 508 may include conductive features and function as the anode. Movement of the grips 506 and 508 relative to the stent 100 changes the contact points. In another example, the body of the grips 506 and 508 may be non-conductive while the features of the grips 506 and 508 may be conductive.

Figure 6:
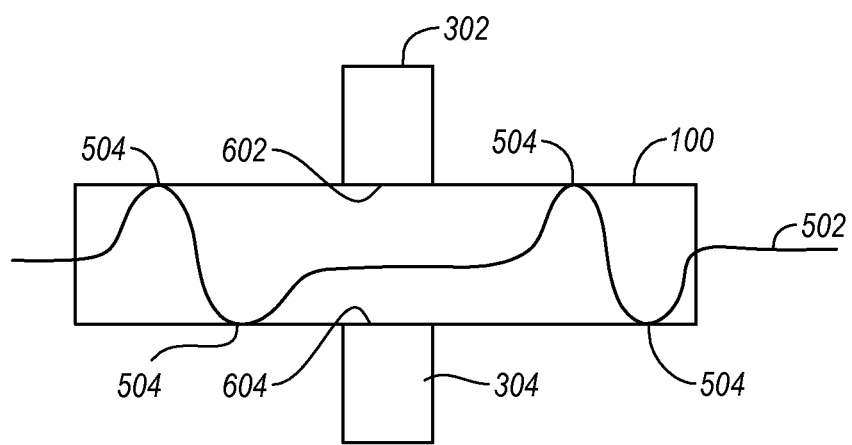
FIG. 6 is a top view illustrating an orientation of the grips of a fixture relative to the stent.

FIG. 6 illustrates a top view of the fixture 308 shown in FIG. 3. In FIG. 6, the grip 302 is disposed directly across the stent 100 from the grip 304. In this manner, relative movement of one or both of the grips 302 and 304 result in rotation of the stent 100 about the anode 502. As the stent 100 rotates due to the movement of the grips 302 and/or 304, the anode 502 remains in contact with an inner surface of the stent 100 at contact points 504. In this example, the anode 502 may not rotate with the stent 100. As a result, the contact points between the anode 502 and the stent 100 change when the stent is repositioned. Similarly, the contact points 602 and 604 between, respectively, the grips 302 and 304 and the outer surface of the stent 100 also change when the stent is repositioned or rotated.

Figure 7A:
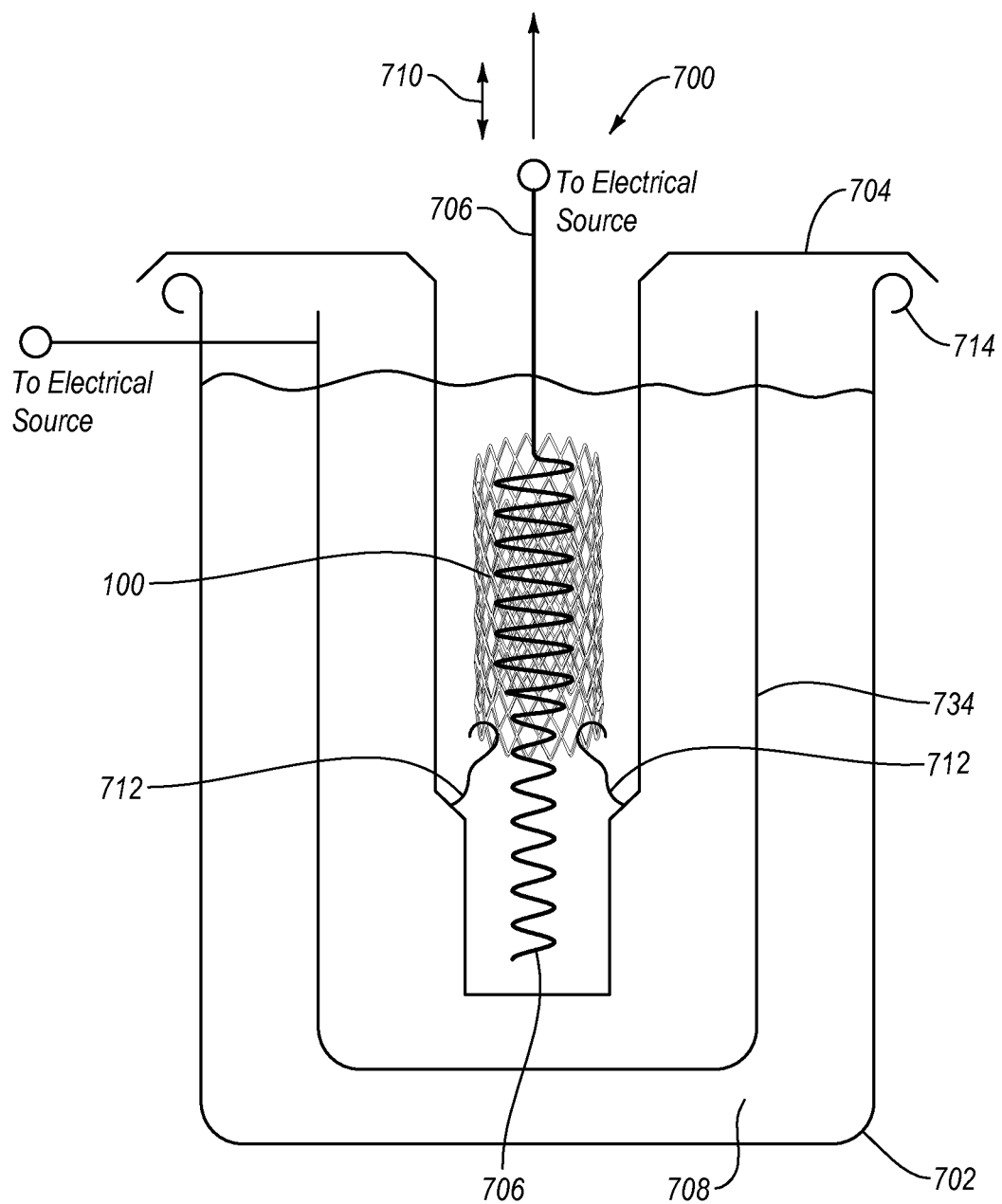
FIG. 7A illustrates another example of an electropolishing fixture that moves the electrode while the stent is held in place.

FIG. 7A illustrates another example of a fixture 700 for electropolishing a device such as a stent. In FIG. 7A, the stent 100 is held in place while an anode 706 is moved. Moving the anode 706 effectively changes the contact points between the stent 100 and the anode 706. This configuration also achieves a more even finish of the stent 100.

FIG. 7A illustrates a container 702 that holds an electrolytic bath 708. The fixture 700 includes a frame 704 that fits within the container 702 during electropolishing. The frame 704, as well as other aspects of the invention such as the grips, may be made from a chemically resistant material such as PTFE, FEP or other fluoro-polymer or glass or ceramic, for example. The frame 704 may removably engage or rest on a rim 714 of the container 702 to provide stabilization during the electropolishing process.

The frame 704 includes a holding mechanism 712 that can removably engage the stent 100 during the electropolishing process and keep the stent 100 substantially in place. The holding mechanism 712, as discussed in more detail below, should prevent the stent from being withdrawn from the bath 708 while the anode is moved to reposition the stent 100 relative to the anode 706. The holding mechanism 712 may include hooks (e.g., platinum or platinum alloy hooks) for instance. The holding mechanism 712 may be conductive or non-conductive.

The stent 100 is loaded on a distal end of the anode 706. The distal end of the anode 706 may have a shape similar to other anodes 706 or electrodes disclosed herein. The anode 706, and other electrodes disclosed herein, may have a coil shape and may have a circular, square, oval, or other cross section. The anode 706 may have dimensions that are substantially the same as or slightly larger than an interior diameter of the stent 100 such that electrical contact between the anode 706 and the stent 100 is established during the electropolishing process. Electrical contact is maintained even as the anode 706 is moved relative to the stent 100.

After the stent 100 is loaded on the anode 706 and after the stent 100 engages the holding mechanism 712, the electropolishing process can begin. During the electropolishing process, the anode 706 may be moved proximally and/or distally as illustrated by the arrow 710. The anode 706 may be withdrawn, for example, by applying a tension on a proximal end of the anode 706 or by attaching the proximal end to a translation mechanism. The anode 706 can then be withdrawn slowly either by hand or under control of a controller in an automated manner using a motor drive for example.

The holding mechanism 712 resists the stent motion and the anode 706 slides within the stent 100. The lateral movement causes the contact points between the anode 706 and the stent 100 to change. As a result, a length of the anode 706 is sufficient to allow the anode 706 to be laterally translated in either direction during the electropolishing process.

In one example, the stent 100 may be surrounded by a collar to prevent the stent from buckling due to longitudinal tension in the stent 100 caused by withdrawal of the anode 706. In another example, a distal tip of the anode 706 may have a decreasing outer diameter to prevent the distal tip from becoming entangled with the stent 100 as the anode 706 is withdrawn from the stent.

FIG. 7A also illustrates a cathode 734. The cathode 734 may be similarly placed and configured in other embodiments disclosed herein. The cathode may be a cylindrical plate or screen or series of rods that is placed, in this example, to be on multiple sides of the stent 100. This allows the current to flow outward from the stent in multiple directions toward the cathode 734. In the examples disclosed herein, the frame 704, collars, or other aspects of the fixtures are arranged such that the electrolyte bath can pass through freely and with minimal obstruction to the electrolyte electric field in the vicinity of the stent.

Figure 7B:
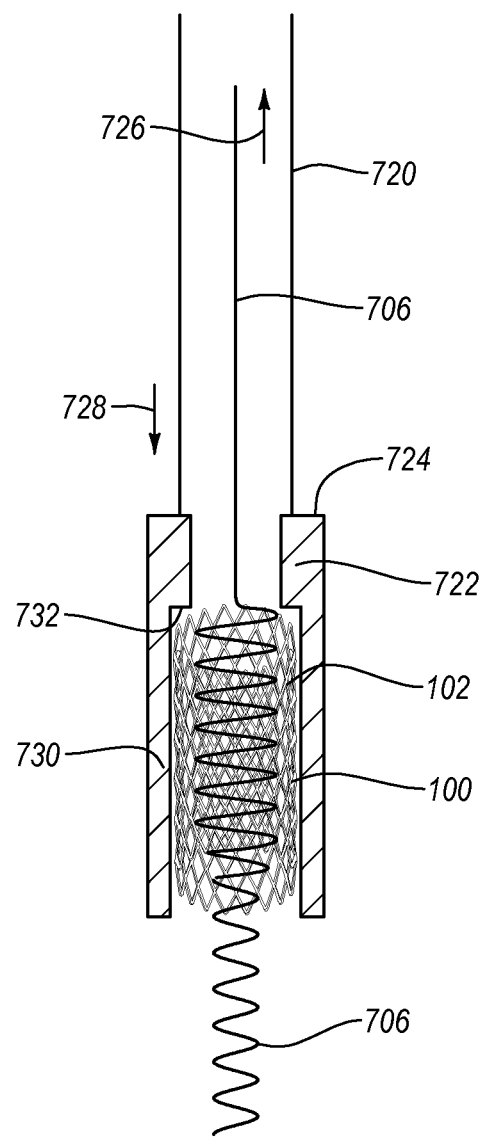
FIG. 7B illustrates a further example of a fixture for moving an electrode relative to a stent during the electropolishing process.

FIG. 7B illustrates another example of a fixture for electropolishing a device such as a stent. In this example, the anode 706 is disposed within a non-conductive tube 720. An end 724 of the tube 720 includes a collar 722. The collar 722 is configured to engage an end 102 of the stent 100 while a body 730 of the collar 722 is configured to protect sides of the stent 100. A lip 732 inside the collar 722 engages the end 102 of the stent 100. As the anode 706 is withdrawn in a proximal direction shown by arrow 726, the tube 720 is held stationary or a force may be exerted in a distal direction shown by an arrow 728 such that the lip 732 prevents the stent 100 from being withdrawn along with the anode 706.

Figure 8:
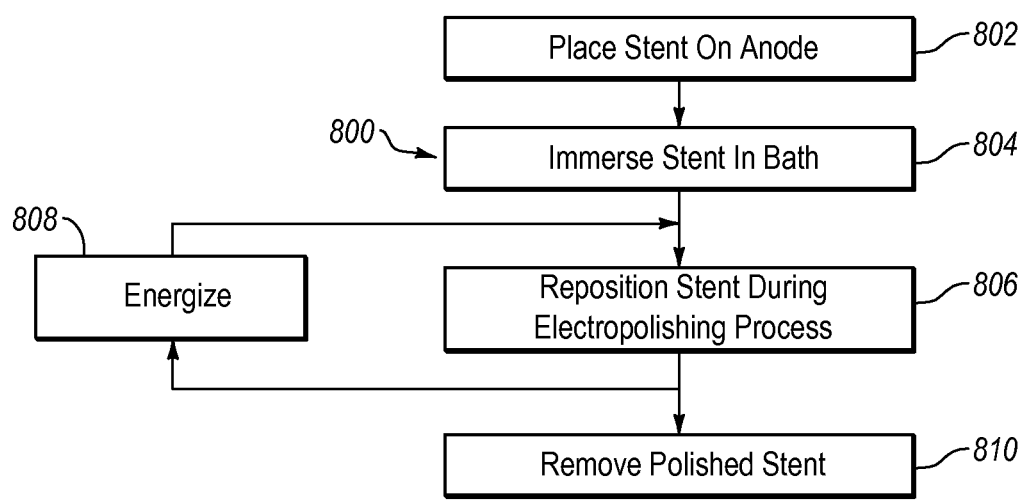
FIG. 8 is a flow diagram illustrating an example of a method for electropolishing a device.

FIG. 8 illustrates a method 800 for electropolishing a device such as a stent. The method 800 begins in box 802 by placing a stent on an anode. This may be done prior to immersing the stent in the electrolytic bath. The stent is placed on the anode in a manner that establishes contact between the anode and the stent. More specifically, in one embodiment, placing the stent on the anode creates contact points between the anode and the stent such that current is able to flow between the stent and the anode.

In box 804, the stent is immersed in an electrolytic bath. As previously described, the anode, cathode, and stent are all immersed in the bath during the electropolishing process. This ensures that the current flows from the stent to the cathode through the electrolytic bath, which allows the electrochemical process to polish the stent, for example by removing material. The ability to electropolish the stent while the stent is immersed also reduces exposure of the stent to an oxidizing environment.

In box 806, the stent may be repositioned during the electropolishing process. During repositioning (or after repositioning) of the stent, the current may continue to flow and is energized in box 808. Alternatively, the current may be turned off during rotation of the stent. The repositioning of the stent 100 can occur periodically, continuously, or as needed. The process of repositioning the stent and of applying current or energizing the system can be repeated until a desired finish is achieved. Advantageously, repositioning the stent in the bath exposes contact points so that the contact points are more effectively polished. The resulting stent has improved dimensions and is more smooth as a result.

In box 810, the polished stent is removed from the electrolytic bath. One of skill in the art can appreciate that the electropolishing systems and methods disclosed herein can be adapted to accommodate multiple stents such that multiple stents can be electropolished at the same time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes, which come within the meaning and range of equivalency of the claims, are to be embraced within their scope.

What is claimed is:

1. A system for electropolishing a device, the system comprising:
   an anode configured to contact the device at contact points;
   a cathode;
   an electrolytic bath, wherein the anode and the cathode are configured to be submerged in the electrolytic bath while the device undergoes an electropolishing process; and
   a fixture configured to reposition the device while the device is immersed in the electrolytic bath wherein the fixture includes a pair of gripping members that include:
      a first grip; and
      a second grip, wherein the first grip and the second grip are configured to engage an external surface of the device together and to reposition the device by relative movement of the first and second grips, and
      wherein the first and second grips include features configured for engaging with the external surface of the device, the features including at least one of teeth, waves, roughness, or texture.

2. The system of claim 1, wherein the anode is configured as a mandrel having one of:
   a size smaller than an inner diameter of the device;
   a size substantially the same as the inner diameter of the device; or
   a size slightly larger than the inner diameter of the device.

3. The system of claim 1, wherein the position includes a controller, the controller configured to move the first grip relative to the second grip to reposition the device.

4. The system of claim 3, wherein repositioning the device exposes the contact point and establishes new contact points between the anode and the device.

5. The system of claim 1, wherein the first and second grip engage the device only when repositioning the device.

6. The system of claim 1, wherein the anode creates the contact points on an inner surface of the device, wherein the fixture repositions the device rotationally.

7. The system of claim 1, wherein the first grip and the second grip are formed from an insulator.

8. A fixture used in subjecting a device to an electropolishing process, the fixture comprising:
   a first grip;
   a second grip, wherein the first grip and the second grip are configured to engage an outer surface of the device at the same time, the device loaded on a mandrel, wherein the first and second grips include a gripping surface configured for engaging with the external surface of the device, the gripping surface including at least one of teeth, waves, roughness, or texture; and
   a controller configured to move at least one of the first grip and the second grip relative to the device to reposition the device relative to an electrical contact point with the device.

9. The fixture of claim 8, wherein the controller moves the first grip relative to the second grip when the gripping surface is engaged with the outer surface to reposition the device and expose the contact point during the electropolishing process, wherein the mandrel is an anode and the contact point is between the device and the anode.

10. The fixture of claim 9, wherein the controller controls movement of the first grip and the second grip such that the device is positioned rotationally around the anode.

11. The fixture of claim 10, wherein the controller is configured to control an orientation and the movement of the first grip independently of an orientation and the movement of the second grip.

12. The fixture of claim 10, wherein the first grip and the second grip are insulated and configured to reposition the device while the device is immersed in an electrolytic bath.

13. The fixture of claim 8, wherein the controller is configured to cause the first grip and the second grip to contact the device only when repositioning the device.

14. The fixture of claim 8, wherein the gripping surface is soft and configured to deform when engaging the outer surface of the device.

15. The fixture of claim 8, wherein the controller is configured to reposition the device periodically, continuously, or in response to manual input.

16. The fixture of claim 8, wherein current is delivered to an outer surface of the device through at least one of the first grip and the second grip.

17. The system of claim 1, further comprising at least a second pair of gripping members that include a third grip and a fourth grip.

* * * * *